(12) United States Patent
Vestweber

(10) Patent No.: US 10,076,332 B2
(45) Date of Patent: Sep. 18, 2018

(54) METHODS FOR APPLYING SURGICAL STAPLES TO INTERNAL WALLS OF HOLLOW TISSUE ORGANS

(71) Applicant: Covidien LP, Mansfield, MA (US)

(72) Inventor: Boris Vestweber, Cologne (DE)

(73) Assignee: Covidien LP, Mansfield, MA (US)

( * ) Notice: Subject to any disclaimer, the term of this patent is extended or adjusted under 35 U.S.C. 154(b) by 244 days.

(21) Appl. No.: 14/996,467

(22) Filed: Jan. 15, 2016

(65) Prior Publication Data

US 2016/0128695 A1 May 12, 2016

Related U.S. Application Data

(63) Continuation of application No. 14/011,103, filed on Aug. 27, 2013, now Pat. No. 9,265,503.

(60) Provisional application No. 61/698,148, filed on Sep. 7, 2012.

(51) Int. Cl.
| | |
|---|---|
| *A61B 17/08* | (2006.01) |
| *A61B 17/115* | (2006.01) |
| *A61B 17/11* | (2006.01) |
| *A61B 17/068* | (2006.01) |
| *A61B 17/10* | (2006.01) |
| *A61B 17/32* | (2006.01) |

(52) U.S. Cl.
CPC ........ *A61B 17/1152* (2013.01); *A61B 17/068* (2013.01); *A61B 17/105* (2013.01); *A61B 17/11* (2013.01); *A61B 17/115* (2013.01); *A61B 17/1155* (2013.01); *A61B 17/32* (2013.01); *A61B 2217/007* (2013.01)

(58) Field of Classification Search
CPC ........... A61B 2017/07214; A61B 2017/07221; A61B 17/07207; A61B 17/115; A61B 17/072; A61B 17/1155; A61B 17/1114; A61B 17/068; A61B 17/105; A61B 17/064; A61B 2017/07271; A61B 2017/2927
USPC ............................. 606/153; 227/175.1–182.1
See application file for complete search history.

(56) References Cited

U.S. PATENT DOCUMENTS

| | | |
|---|---|---|
| 4,473,077 A | 9/1984 | Noiles et al. |
| 4,576,167 A | 3/1986 | Noiles |
| 4,646,745 A | 3/1987 | Noiles |
| 5,005,749 A | 4/1991 | Aranyi |
| 5,119,983 A | 6/1992 | Green et al. |

(Continued)

FOREIGN PATENT DOCUMENTS

| | | |
|---|---|---|
| DE | 102007057207 A1 | 5/2009 |
| DE | 202011101205 U1 | 8/2012 |
| EP | 1652481 A2 | 5/2006 |

OTHER PUBLICATIONS

European Search Report dated Dec. 11, 2013 from counterpart EP Application No. EP13183338.6 (8 pgs).

*Primary Examiner* — Katherine M Shi

(57) ABSTRACT

A method of performing a surgical anastomosis is disclosed. The method includes providing an anastomotic device including a fluid supply channel extending between a handle assembly and a head assembly. The method also includes positioning the head assembly of the anastomotic device adjacent a hollow tissue organ, inserting the head assembly of the anastomotic device into the hollow tissue organ, and discharging an inflation fluid through at least one fluid outlet and into the hollow tissue organ to insufflate at least a portion of the hollow tissue organ.

11 Claims, 3 Drawing Sheets

(56) References Cited

U.S. PATENT DOCUMENTS

| | | |
|---|---|---|
| 5,403,326 A | 4/1995 | Harrison et al. |
| 5,483,951 A | 1/1996 | Frassica et al. |
| 5,588,579 A | 12/1996 | Schnut et al. |
| 5,868,760 A | 2/1999 | McGuckin, Jr. |
| 6,053,390 A | 4/2000 | Green et al. |
| 6,083,241 A | 7/2000 | Longo et al. |
| 6,102,271 A | 8/2000 | Longo et al. |
| 6,119,913 A | 9/2000 | Adams et al. |
| 6,126,058 A | 10/2000 | Adams et al. |
| 6,142,933 A | 11/2000 | Longo et al. |
| 6,179,195 B1 | 1/2001 | Adams et al. |
| 6,241,140 B1 | 6/2001 | Adams et al. |
| 6,264,086 B1 | 7/2001 | McGuckin, Jr. |
| 6,302,311 B1 | 10/2001 | Adams et al. |
| 6,343,731 B1 | 2/2002 | Adams et al. |
| 6,451,029 B1 | 9/2002 | Yeatman |
| 6,478,210 B2 | 11/2002 | Adams et al. |
| 6,585,144 B2 | 7/2003 | Adams et al. |
| 6,601,749 B2 | 8/2003 | Sullivan et al. |
| 6,629,630 B2 | 10/2003 | Adams |
| 6,632,227 B2 | 10/2003 | Adams |
| 6,695,198 B2 | 2/2004 | Adams et al. |
| 6,820,791 B2 | 11/2004 | Adams |
| 6,827,246 B2 | 12/2004 | Sullivan et al. |
| 6,840,423 B2 | 1/2005 | Adams et al. |
| 6,866,178 B2 | 3/2005 | Adams et al. |
| 6,874,669 B2 | 4/2005 | Adams et al. |
| 6,959,851 B2 | 11/2005 | Heinrich |
| 7,083,630 B2 | 8/2006 | DeVries et al. |
| 7,090,684 B2 | 8/2006 | McGuckin, Jr. et al. |
| 7,810,690 B2 | 10/2010 | Bilotti et al. |
| 8,181,840 B2 | 5/2012 | Milliman |
| 9,265,503 B2 | 2/2016 | Vestweber |
| 2002/0020732 A1 | 2/2002 | Adams et al. |
| 2002/0047036 A1 | 4/2002 | Sullivan et al. |
| 2002/0063143 A1 | 5/2002 | Adams et al. |
| 2003/0019905 A1 | 1/2003 | Adams et al. |
| 2003/0127491 A1 | 7/2003 | Adams et al. |
| 2003/0132267 A1 | 7/2003 | Adams et al. |
| 2003/0144675 A1 | 7/2003 | Nicolo |
| 2003/0192937 A1 | 10/2003 | Sullivan et al. |
| 2004/0134964 A1 | 7/2004 | Adams et al. |
| 2004/0193184 A1 | 9/2004 | Laufer et al. |
| 2004/0232198 A1 | 11/2004 | Adams et al. |
| 2005/0145675 A1 | 7/2005 | Hartwick et al. |
| 2005/0205640 A1 | 9/2005 | Milliman |
| 2006/0108393 A1* | 5/2006 | Heinrich .......... A61B 17/00491 227/179.1 |
| 2006/0151568 A1 | 7/2006 | Weller et al. |
| 2006/0155308 A1 | 7/2006 | Griego |
| 2006/0191975 A1 | 8/2006 | Adams et al. |
| 2006/0241692 A1 | 10/2006 | McGuckin et al. |
| 2007/0023475 A1 | 2/2007 | Csiky |
| 2007/0233161 A1 | 10/2007 | Weller et al. |
| 2008/0004566 A1 | 1/2008 | Sloan |
| 2010/0163598 A1 | 7/2010 | Belzer |

* cited by examiner

METHODS FOR APPLYING SURGICAL STAPLES TO INTERNAL WALLS OF HOLLOW TISSUE ORGANS

CROSS-REFERENCE TO RELATED APPLICATION

This application is a continuation of U.S. patent application Ser. No. 14/011,103 filed Aug. 27, 2013, which claims benefit of and priority to U.S. Provisional Application No. 61/698,148 filed Sep. 7, 2012, and the disclosures of each of the above-identified applications are hereby incorporated by reference in their entirety.

BACKGROUND

Technical Field

The present disclosure relates generally to methods for applying surgical staples to body tissue. More particularly, the present disclosure relates to an anastomotic device suitable for performing circular anastomosis and/or treatment to internal walls of hollow tissue organs.

Background of Related Art

Anastomosis is the surgical joining of separate hollow organ sections. Typically, an anastomosis procedure follows surgery in which a diseased or defective section of hollow tissue is removed and the remaining end sections are to be joined. Depending on the desired anastomosis procedure, the end sections may be joined by either circular, end-to-end, or side-to-side organ reconstruction methods.

In a circular anastomosis procedure, the two ends of the organ sections are joined by means of a stapling instrument which drives a circular array of staples through the end section of each organ section and cores any tissue within the driven circular array of staples to free the tubular passage. Examples of instruments for performing circular anastomosis of hollow organs are described in U.S. Pat. Nos. 6,053,390, 5,588,579, 5,119,983, 5,005,749, 4,646,745, 4,576,167, and 4,473,077, each of which is incorporated herein in its entirety by reference. Typically, these instruments include an elongated shaft having a handle portion at a proximal end to actuate the instrument and a staple holding component (e.g., a cartridge assembly) disposed at a distal end. An anvil assembly including an anvil rod with attached anvil head is mounted to the distal end of the instrument adjacent the staple holding component. Opposed end portions of tissue of the hollow organ(s) to be stapled are clamped between the anvil head and the staple holding component. The clamped tissue is stapled by driving one or more staples from the staple holding component so that the ends of the staples pass through the tissue and are deformed by the anvil head. An annular knife is advanced to core tissue within the hollow organ to free a tubular passage within the organ.

Besides anastomosis of hollow organs, surgical stapling devices for performing circular anastomosis have been used to treat internal hemorrhoids in the rectum. Typically, during use of a circular stapling device for hemorrhoid treatment, the anvil head and the staple holding component of the surgical stapling device are inserted through the anus and into the rectum with the anvil head and the staple holding component in an open or unapproximated position. Thereafter, a pursestring suture is used to pull the internal hemorrhoidal tissue towards the anvil rod. Next, the anvil head and the staple holding component are approximated to clamp the hemorrhoid tissue between the anvil head and the staple holding component. The stapling device is fired to remove the hemorrhoidal tissue and staple the cut tissue.

SUMMARY

The present disclosure relates to a method of performing a surgical anastomosis. The method comprises providing an anastomotic device including a handle assembly, an elongated body portion extending distally from the handle assembly, a head assembly and a fluid supply channel. The head assembly is disposed adjacent a distal portion of the elongated body portion, and includes an anvil assembly and a cartridge assembly. The fluid supply channel extends between the handle assembly and the head assembly. At least one fluid outlet is disposed at a distal end of the fluid supply channel. The method further comprises positioning the head assembly of the anastomotic device adjacent a hollow tissue organ, inserting the head assembly of the anastomotic device into the hollow tissue organ, and discharging an inflation fluid through the at least one fluid outlet and into the hollow tissue organ to insufflate at least a portion of the hollow tissue organ.

In disclosed embodiments, discharging an inflation fluid comprises discharging the inflation fluid through the at least one fluid outlet and into an intestine to insufflate a rectal stump. It is further disclosed to discharge the inflation fluid through the at least one fluid outlet and into the hollow tissue organ while inserting the head assembly of the anastomotic device into the hollow tissue organ. It is further disclosed to move the head assembly distally beyond a sphincter muscle, and to discharge the inflation fluid through the at least one fluid outlet and into the hollow tissue after the head assembly of the anastomotic device has been moved distally beyond the sphincter muscle.

In disclosed embodiments, discharging an inflation fluid comprises discharging between about 0.60 oz and about 17.0 oz of the inflation fluid through the at least one fluid outlet. It is also envisioned to discharge between about 1.0 oz and about 11.0 oz of the inflation fluid through the at least one fluid outlet.

In disclosed embodiments, the cartridge assembly includes staples therein, and the method further comprises ejecting staples from the cartridge assembly toward the anvil assembly and creating a staple line in the hollow tissue organ.

In disclosed embodiments, discharging an inflation fluid comprises discharging the inflation fluid through the at least one fluid outlet at a rate in the range of between about 00.01 oz/s and about 0.70 oz/s. It is also envisioned to discharge between about 0.03 oz/s and about 0.34 oz/s of the inflation fluid through the at least one fluid outlet.

In disclosed embodiments, discharging an inflation fluid comprises discharging the inflation fluid through the at least one fluid outlet at a distal face of the cartridge assembly. It is further envisioned to discharge the inflation fluid through the at least one fluid outlet while a retaining pin, which interconnects the cartridge assembly and anvil assembly, is in a fully retracted position. It is also envisioned to discharge the inflation fluid through the at least one fluid outlet at a distal end of a guide lumen arranged concentric to the cartridge assembly.

In disclosed embodiments, the anastomotic device includes a knife disposed at least partially within the head assembly, and the method further comprises advancing the knife to cut tissue of the hollow tissue organ. It is envisioned that the inflation fluid is discharged through the at least one fluid outlet at an annular space between the knife and a lateral wall of the head section.

DESCRIPTION OF THE DRAWINGS

Embodiments of a surgical stapling device and method of use are disclosed herein with reference to the drawings, wherein.

DETAILED DESCRIPTION

Embodiments of the presently disclosed anastomotic device will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component farther away from the user.

Figure 1:
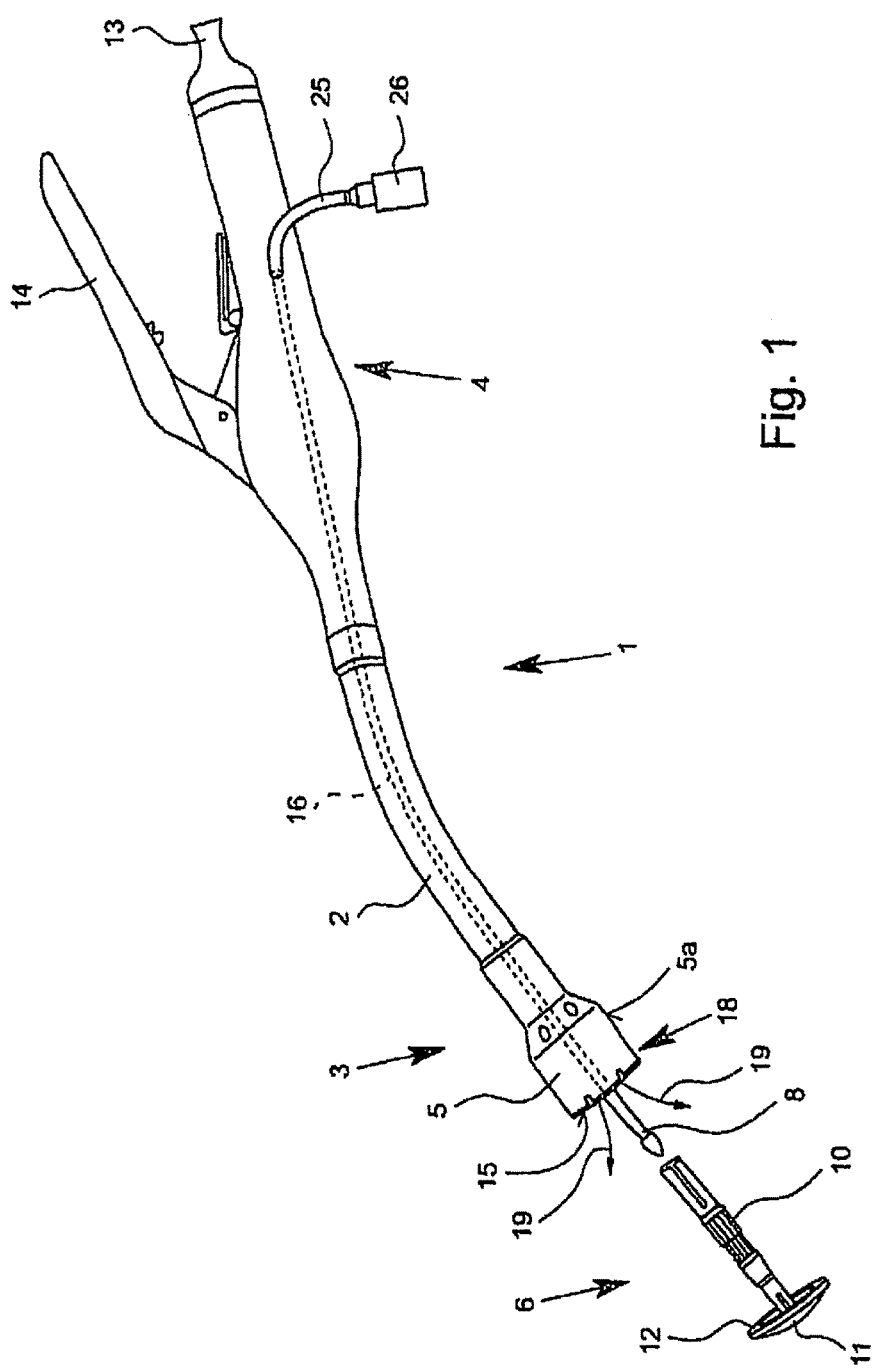
FIG. 1 is a side view of an anastomotic device according to embodiments of the present disclosure.

FIG. 1 illustrates an embodiment of an anastomotic device according to the present disclosure, referenced generally as reference numeral 1. Anastomotic device 1 is configured for forming an anastomosis, e.g., an intestinal anastomosis. Anastomotic device 1 includes a handle assembly or actuating part 4, an elongated body portion or introducer sheath 2 extending distally from actuating part 4, and a shell assembly or head section 3 mounted adjacent a distal end of introducer sheath 2. Actuating part 4 includes a fixed handle and a moveable handle, trigger or operating grip 14. Actuating part 4 also includes an approximation knob or adjusting screw 13 for moving a thrust bearing part, anvil section or anvil assembly 6 relative to a cartridge assembly of head section 3. A head assembly includes anvil assembly 6 and the cartridge assembly.

Figure 2:
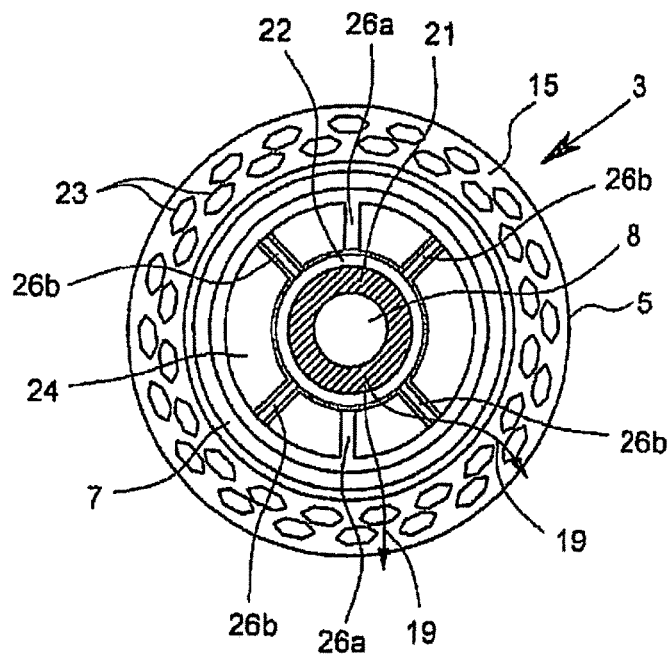
FIGS. 2-4 are cross-sectional views of a head section of the anastomotic device of FIG. 1 in accordance with various embodiments of the present disclosure.
Figure 3:
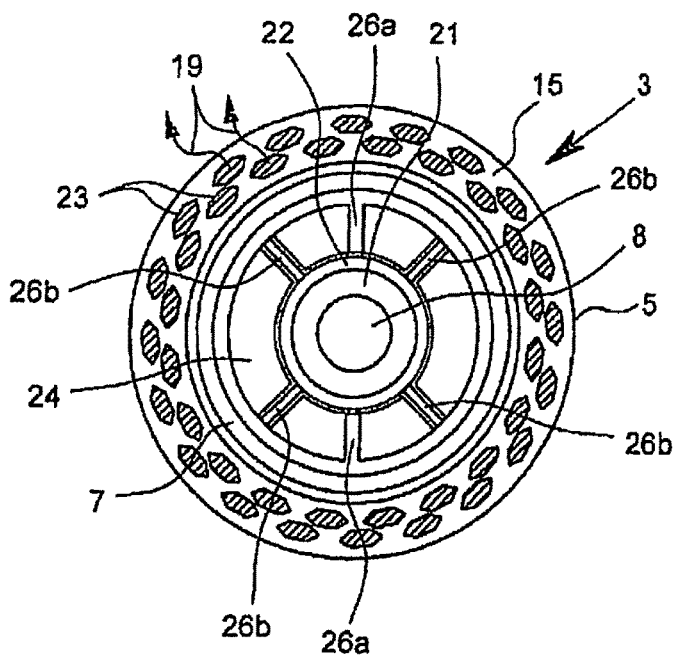
Figure 4:
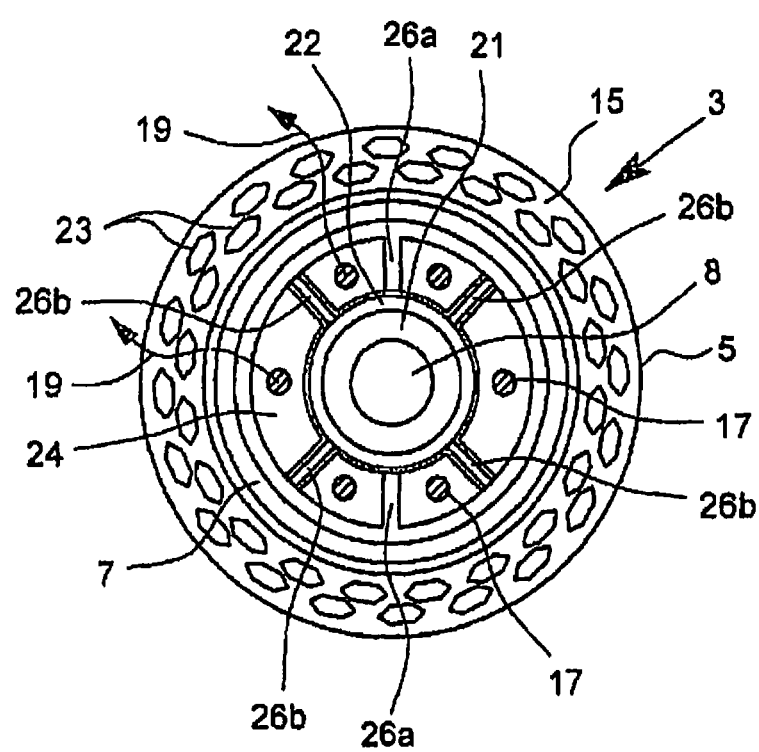

Head section 3 includes a distal hollow-cylindrical head section 5, which houses a clamping mechanism (or stapling mechanism) and a plurality of staples. During clamping or stapling, the clamps or staples (not shown) of head section 3 are moved toward anvil assembly 6. Additionally, an annular or ring-shaped extendable and retractable knife 7 and a retaining pin 8 are arranged within head section 3. Retaining pin 8 can be extended and retracted into head section 3. Knife 7 and retaining pin 8 are arranged concentrically within hollow-cylindrical head section 5, and retaining pin 8 is arranged centrically in head section 3 within a sleeve 22. With reference to FIGS. 2-4, knife 7 is shown mechanically engaged with a pusher part 24. Pusher part 24 includes two guide webs 26a, and additional guide webs 26b that extend radially outward from sleeve 22.

As shown in FIG. 1, retaining pin 8 is connectable to a shaft or vertical passageway 10 of anvil assembly 6. Further, shaft 10 is connected to and extends proximally from an anvil 11 of anvil assembly 6. On a proximal side of anvil 11 (i.e., the side facing head section 3), anvil 11 includes a circular anvil surface 12 with staple-forming pockets. The connection of retaining pin 8 and anvil assembly 6 can take place by snapping retaining pin 8 into shaft 10, for example.

Retaining pin 8 is extended and retracted by turning adjusting screw 13 at the proximal end of actuating part 4. Actuation of operating grip 14 causes the stapling mechanism to be actuated and causes distal advancement of knife 7.

It is disclosed that anastomotic device 1 is used for producing an intestinal anastomosis. After removing a diseased part of the large intestine, for example, it is necessary to join the remaining proximal portion and the distal portion of the large intestine. During such a procedure, anvil assembly 6 is positioned into a first portion of the large intestine. This portion of the large intestine surrounds anvil 11, while shaft 10 extends proximally from this portion of the large intestine. Subsequently, anastomotic device 1 is inserted, with retaining pin 8 in a retracted position, through the anus and pushed to a second portion of the intestine that has been sealed. Then, retaining pin 8 is extended to an extended position (as shown in FIG. 1) and punctures the second portion of the intestine (e.g., a sutured portion).

After connecting retaining pin 8 with shaft 10 of anvil assembly 6, anvil assembly 6 is moved proximally by retracting retaining pin 8 into head section 3 until the first and second portions of the intestine lie close together. The stapling mechanism is then activated, such that the staples are ejected from a circular front surface 15 of head section 5 and are moved against the facing circular anvil surface 12 causing deformation of the staples such that the two intestine portions are interconnected. Actuation of operating grip 14 also causes knife 7 to extend from head section 3 to separate tissue located between head section 3 and anvil assembly 6. After tissue is stapled and cut, anastomotic device 1 can then be retracted from the body through the anal canal, for example. DE 10 2007 057 207 A1 discloses a method with the features as described above and a clamp inserter.

Deviating from the clamp inserter as known from DE 10 2007 057 207 A1, anastomotic device 1, as shown in FIG. 1, is configured to deliver an inflation fluid, such as liquid 19, via a fluidic connection between actuating part 4 and head section 3 into the body lumen and thus, effect an inflation or insufflation of the body tissue. One of skill in the art will recognize that inflation fluid may comprise a liquid or a gas, or any combination thereof. Filling the body lumen with inflation liquid 19 causes an increase in volume, which facilitates a friction-free and an injury-free insertion of anastomotic device 1 into the body lumen, for example through the anal canal into a portion of the large intestine. Additionally, inflating the body lumen can be helpful prior to conducting an anastomosis in providing a leak test of sutured tissue. It is envisioned that using a colored inflation liquid will allow a visual control during insertion of anastomotic device 1 and during the leak test of the suture, wherein it is determined whether and to what extent a liquid has penetrated the suture.

Anastomotic device 1 of the present disclosure includes at least one fluid outlet disposed at the end (e.g., a distal end) of fluid supply channel 16. The configuration of the fluidic connection allows inflation liquid 19 to be discharged from anastomotic device 1 during insertion of head section 3 into the body lumen, for example. It is further disclosed that during an intestinal anastomosis, inflation liquid 19 can be discharged from anastomotic device 1 after a distal boundary region 18 of head section 3 has passed the sphincter muscle, and/or when pushing introducer sheath 2 distally.

As shown in FIG. 1, inflation liquid 19 can be delivered when at least a portion of retaining pin 8 is extended distally beyond head section 3. Because the retaining pin 8 is typically fully retracted into head section 3 during insertion of anastomotic device 1 into the body lumen, the fluidic connection is also configured for the delivery of inflation liquid 19 into the body lumen when retaining pin 8 is partially and/or completely retracted. In the retracted condition, the distal tip of retaining pin 8 is arranged inside the head section 3.

The delivery of inflation liquid 19 into the body lumen via circular front surface 15 of head section 5 or a distal face of head section 3 can be helpful, for example, to inflate a collapsed body lumen. It is envisioned that inflation liquid 19 is delivered into the intestine to insufflate the rectal stump. It is further envisioned that inflation liquid 19 is delivered through the fluid outlet(s) and into the hollow tissue organ while inserting the head assembly (e.g., head section 3) of anastomotic device 1 into the hollow tissue organ.

With particular reference to FIG. 2, retaining pin 8 is positioned within a guide lumen 21 arranged concentric to head section 3. In this embodiment, inflation liquid 19 exits through a fluid outlet at the distal end of guide lumen 21. In the illustrated embodiment, the radial inner boundary of guide lumen 21 is retaining pin 8, and the radial outer boundary of guide lumen 21 is sleeve 22.

An alternative embodiment of anastomotic device 1 is shown in FIG. 3. Here, the delivery of inflation liquid 19 takes place through staple-receiving pockets or clamp outlets 23 of the stapling mechanism in circular front surface 15 of head section 5. It is further envisioned that additional fluid outlets (not shown) may be provided in front surface 15, so that the liquid delivery does not take place through clamp outlets 23.

Another alternative embodiment of anastomotic device 1 is shown in FIG. 4. Here, the delivery of inflation liquid 19 takes place through fluid outlets 17 in the annular space between knife 7 and sleeve 22. It is further envisioned that inflation liquid 19 can be delivered through fluid outlets 17 in side walls of pusher part 24. Alternatively and/or additionally, inflation liquid 19 can be delivered through gaps between the side walls of pusher part 24 and sleeve 22 and/or guide webs 26b.

It is further envisioned that a lateral portion of head section 3, e.g., within distal boundary region 18, include one or more fluid outlets which may be evenly distributed in a circumferential direction. Here, inflation liquid 19 can be delivered through a distal lateral surface 5a (FIG. 1) of head section 5.

In the disclosed embodiments including more than one fluid outlet, it is envisioned that a distal portion of fluid supply channel 16 branches off into the fluid outlets.

Additionally, and as shown in FIG. 1, a hose 25 extends from actuating part 4 and is connected to and/or forms a proximal portion of fluid supply channel 16. It is envisioned that hose 25 is connected to a reservoir (not shown) containing inflation liquid 19. In the illustrated embodiment, hose 25 includes a screw-type cap 26 at its free end, so that it is possible after unscrewing screw-type cap 26 to inject inflation liquid 19 into hose 25 with a syringe or the like. A syringe may be further used to force inflation liquid 19 through fluid supply channel 16, toward head section 3, and out of the fluid outlet(s) (e.g., fluid outlets 17). It is further envisioned that a three-way connection is provided to facilitate the supply of different liquids through hose 25 and fluid supply channel 16.

It is envisioned that between about 0.60 oz and about 17.0 oz of inflation liquid 19 is discharged through the fluid outlet(s). In embodiments, between about 1.0 oz and about 11.0 oz of inflation liquid 19 is discharged through the fluid outlet(s). It is further envisioned that the amount of inflation liquid 19 that is used is at least partially determined by the bursting pressure of the hollow tissue organ (e.g., within or adjacent a rectal stump) near the staple line, such that the amount of inflation liquid 19 used does not cause the pressure in the hollow tissue organ near the staple line to exceed the bursting pressure. The use of a pressure sensor or other conventional methods can be used to determine the actual pressure.

It is further envisioned that inflation liquid 19 is discharged through the fluid outlet(s) at a rate of between about 0.01 oz/s and about 0.70 oz/s. In embodiments, inflation liquid 19 is discharged through the fluid outlet(s) at a rate of between about 0.03 oz/s and about 0.34 oz/s.

It is further envisioned that anastomotic device 1 is inserted into and/or retracted from the body lumen at a rate of between about 0.03 in/s and about 4.0 in/s. In embodiments, anastomotic device 1 is inserted into and/or retracted from the body lumen at a rate of between about 0.10 in/s and about 2.0 in/s.

Persons skilled in the art will understand that the various apparatus, and corresponding methods of use described herein, and shown in the accompanying drawings, constitute non-limiting, exemplary embodiments of the present disclosure, and that additional components and features may be added to any of the embodiments discussed herein above without departing from the scope of the present disclosure.

Additionally, persons skilled in the art will understand that the elements and features shown or described in connection with one exemplary embodiment may be combined with those of another embodiment without departing from the scope of the present disclosure, and will appreciate further features and advantages of the presently disclosed subject matter based on the above-described embodiments and the claims. Accordingly, the present disclosure is not limited by what has been particularly shown and described.

The invention claimed is:

1. An anastomotic device, comprising:
   a handle assembly;
   an elongated body portion extending distally from the handle assembly and defining a longitudinal axis;
   a head assembly disposed adjacent a distal portion of the elongated body portion, the head assembly including an anvil assembly and a cartridge assembly;
   a retaining member extending at least partially through the cartridge assembly and being configured to mechanically engage the anvil assembly;
   a guide lumen disposed at least partially within the cartridge assembly, at least a portion of the retaining member is disposed within at least a portion of the guide lumen;
   a channel extending between the handle assembly and a portion of the head assembly, a portion of the channel being in fluid contact with the guide lumen;
   an annular knife disposed at least partially within the head assembly, the annular knife being longitudinally movable with respect to the cartridge assembly;
   an annular space defined between the annular knife and a lateral wall of the head assembly; and
   at least one outlet disposed adjacent a distal end of the channel, in the annular space, and in contact with the guide lumen.

2. The anastomotic device according to claim 1, wherein the anvil assembly is longitudinally movable with respect to the cartridge assembly.

3. The anastomotic device according to claim 1, wherein the cartridge assembly includes staples therein.

4. The anastomotic device according to claim 1, wherein the at least one outlet is disposed on a distal face of the cartridge assembly.

5. The anastomotic device according to claim 1, wherein the retaining member is proximally and distally movable with respect to the cartridge assembly.

6. The anastomotic device according to claim 1, where a first boundary of the guide lumen is the retaining member.

7. The anastomotic device according to claim 6, wherein the first boundary of the guide lumen is a radial inner boundary.

8. The anastomotic device according to claim 7, wherein a radial outer boundary of the guide lumen is a sleeve.

9. The anastomotic device according to claim 8, wherein the sleeve is the closest wall of the head assembly to the retaining member.

10. The anastomotic device according to claim 6, wherein a second boundary of the guide lumen is a sleeve.

11. The anastomotic device according to claim 10, wherein the sleeve is the closest wall of the head assembly to the retaining member.

\* \* \* \* \*